United States Patent
Cooke et al.

(10) Patent No.: US 9,029,396 B2
(45) Date of Patent: May 12, 2015

(54) SUBSTITUTED INDOLE DERIVATIVES

(71) Applicants: Nigel Graham Cooke, Oberwil (CH); Rita Ramos, Allschwil (CH); Karen Kammertoens, Village-Neuf (FR); Maurice Van Eis, St. Louis (FR)

(72) Inventors: Nigel Graham Cooke, Oberwil (CH); Rita Ramos, Allschwil (CH); Karen Kammertoens, Village-Neuf (FR); Maurice Van Eis, St. Louis (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/194,879

(22) Filed: Mar. 3, 2014

(65) Prior Publication Data
US 2014/0179634 A1 Jun. 26, 2014

Related U.S. Application Data

(62) Division of application No. 13/471,512, filed on May 15, 2012, now Pat. No. 8,703,782.

(60) Provisional application No. 61/486,808, filed on May 17, 2011.

(51) Int. Cl.
| | | |
|---|---|---|
| *C07D 215/04* | (2006.01) | |
| *A61K 31/47* | (2006.01) | |
| *A61K 31/499* | (2006.01) | |
| *C07D 401/14* | (2006.01) | |
| *C07F 9/6558* | (2006.01) | |
| *A61K 31/675* | (2006.01) | |

(52) U.S. Cl.
CPC ............ *A61K 31/499* (2013.01); *C07D 401/14* (2013.01); *C07F 9/65583* (2013.01); *A61K 31/675* (2013.01)

(58) Field of Classification Search
USPC .................... 544/283, 284; 514/266.1, 266.2
See application file for complete search history.

(56) References Cited

U.S. PATENT DOCUMENTS

| 4,925,860 A | 5/1990 | Herbranson et al. |
|---|---|---|
| 8,703,782 B2 | 4/2014 | Cooke et al. |
| 2005/0203068 A1 | 9/2005 | Wingard et al. |
| 2007/0203236 A1 | 8/2007 | Smith et al. |

FOREIGN PATENT DOCUMENTS

| CN | 101812097 A | 8/2010 |
|---|---|---|
| WO | 91/13070 A1 | 9/1991 |
| WO | 00/08033 A1 | 2/2000 |
| WO | 01/27106 A1 | 4/2001 |
| WO | 2003057153 A2 | 7/2003 |
| WO | 2003059255 A2 | 7/2003 |
| WO | 03082859 A1 | 10/2003 |
| WO | 2004083202 A1 | 9/2004 |
| WO | 2006078846 A1 | 7/2006 |
| WO | 20071008514 A2 | 1/2007 |
| WO | 2007/107318 A1 | 9/2007 |
| WO | 2008064274 A1 | 5/2008 |
| WO | 2011057204 A2 | 5/2011 |

OTHER PUBLICATIONS

Elworthy et al., "Orally bioavailable prodrugs of a BCS class 2 molecule, an inhibitor of HIV-1 reverse transcriptase," Bioorg. Med. Chem. Lett. 18:6344-6347 (2008).

Chassaing et al., "Highly Water-Soluble Prodrugs of Anthelmintic Benzimidazole Carbamates: Synthesis, Pharmacodynamics, and Pharmacokinetics," J. Med. Chem. 51:1111-1114 (2008).

Kumpulainen et al., "Synthesis, in vitro and in vivo characterization of novel ethyl dioxy phosphate prodrug of propofol," European Journal of Pharmaceutical Sciences 34:110-117 (2008).

Teicher, Beverly A., "Protein Kinase C as a Therapeutic Target," Clin Cancer Res 2006; 12(18):5336-5345.

Skvara et al., "The PKC inhibitor AEB071 may be a therapeutic option for psoriasis," The Journal of Clinical Investigation, vol. 118, No. 9, Sep. 2008, pp. 3151-3159.

Fang et al., "The Effects of AEB071 (Sotrastaurin) with Tacrolimus on Rat Heterotopic Cardia Allograft Rejection and Survival," Journal of Surgical Research, vol. 171, No. 1, Nov. 2011, pp. e133-e137.

*Primary Examiner* — Paul V Ward
(74) *Attorney, Agent, or Firm* — Sophie Binet Cross

(57) ABSTRACT

The present invention relates to substituted indole derivatives, to processes for their production, their use as pharmaceuticals and to pharmaceutical compositions comprising them.

7 Claims, 2 Drawing Sheets

SUBSTITUTED INDOLE DERIVATIVES

This application is a divisional application of U.S. patent application Ser. No. 13/471,512 filed on May 15, 2012, which claims benefit under 35 U.S.C. §119(e) of U.S. Provisional Application No. 61/486,808 filed May 17, 2011; the contents of which is incorporated herein by reference in their entirety.

The present invention relates to substituted indole derivatives, to processes for their production, their use as pharmaceuticals and to pharmaceutical compositions comprising them.

BACKGROUND OF THE INVENTION

Poor bioavailability of drug products is frequently a limiting factor for pharmaceutically effective ingredients. This problem is now addressed in a particular field of indole derivatives by converting a corresponding parent drug into a derivative thereof, which appears to have unexpected favorable effects as compared to its parent compounds.

SUMMARY OF THE INVENTION

Specifically, the present invention relates to a compound of formula (I) or a pharmaceutically acceptable salt or hydrate thereof,

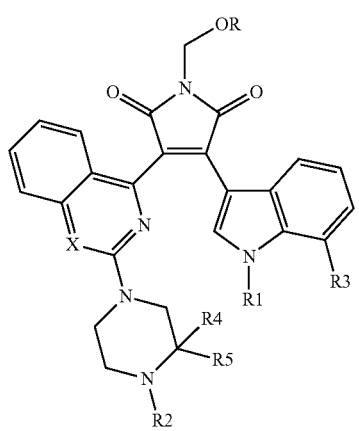

(I)

wherein
X is CH or N;
R is H or $PO_3H_2$;
R1 is H; or $C_{1-4}$alkyl;
R2 is H; or $C_{1-4}$alkyl;
R3 is H; $C_{1-4}$alkyl; CN; Hal; or OH; and
R4 and R5 are independently from each other H, or $C_{1-4}$alkyl; or R4 and R5 form together with the carbon atom to which they are attached a 3-6 membered cycloalkyl group.

In another embodiment the present invention relates to a compound of formula (I) or a pharmaceutically acceptable salt or hydrate thereof,
wherein
X is CH;
R is $PO_3H_2$;
R1 is H;
R2 is H; or $C_{1-4}$alkyl;
R3 is H; or $C_{1-4}$alkyl; and
R4 and R5 are independently from each other H; or R4 and R5 form together with the carbon atom to which they are attached a 3-6 membered cycloalkyl group.

In another embodiment the present invention relates to a compound of formula (I) or a pharmaceutically acceptable salt or hydrate thereof,
wherein
X is CH;
R is H;
R1 is H;
R2 is H; or $C_{1-4}$alkyl;
R3 is H; or $C_{1-4}$alkyl; and
R4 and R5 are independently from each other H; or R4 and R5 form together with the carbon atom to which they are attached a 3-6 membered cycloalkyl group.

In another embodiment the present invention relates to a compound of formula (I) or a pharmaceutically acceptable salt or hydrate thereof,
wherein
X is N;
R is $PO_3H_2$;
R1 is H;
R2 is H; or $C_{1-4}$alkyl;
R3 is H; and
R4 and R5 are independently from each other H; or R4 and R5 form together with the carbon atom to which they are attached a 3-6 membered cycloalkyl group.

In another embodiment the present invention relates to a compound of formula (I) or a pharmaceutically acceptable salt or hydrate thereof,
wherein
X is N;
R is $PO_3H_2$;
R1 is H;
R2 is H; or $C_{1-4}$alkyl;
R3 is H; and
R4 and R5 are independently from each other H; or $C_{1-4}$alkyl.

In another embodiment the invention relates to a compound of formula (II)

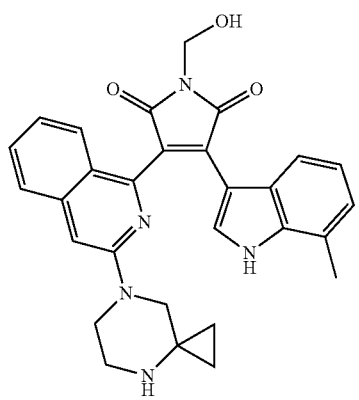

(II)

or a pharmaceutically acceptable salt thereof.

In another embodiment the invention relates to a compound of formula (III)

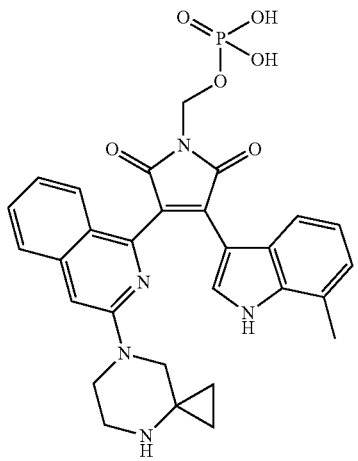

(III)

or a pharmaceutically acceptable salt or hydrate thereof.

In another embodiment the invention relates to a compound of formula (IV)

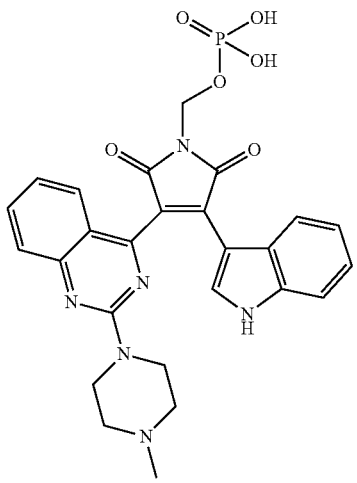

(IV)

or a pharmaceutically acceptable salt thereof.

DETAILED DESCRIPTION OF THE DRAWINGS

PRIOR ART

Figure 1:
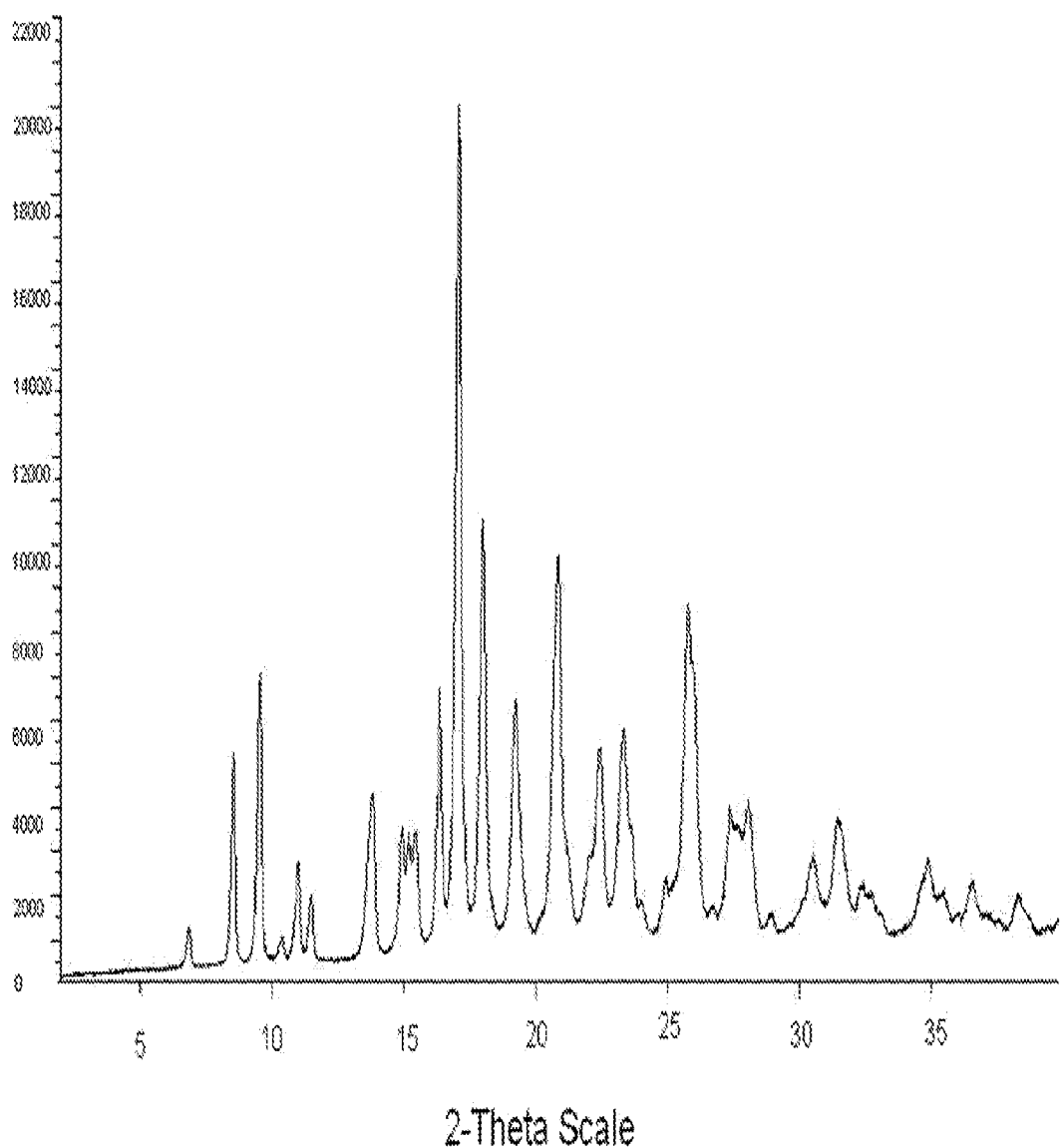
FIG. 1 shows the X-ray diffractogram of the crystalline monohydrate of phosphoric acid mono-[3-[3-(4,7-diazaspiro[2.5]oct-7-yl)-isoquinolin-1-yl]-4-(7-methyl-1H-indol-3-yl)-2,5-dioxo-2,5-dihydro-pyrrol-1-ylmethyl]ester (monhydrate of Example No 1).

N. Fotouhi et al. (EP 1,224,181) describe substituted pyrrole derivatives wherein the chemical modification on said pyrrole ring consists of a large number of variables and may also contain a methylene hydroxy or a methylene phosphate group.

DEFINITIONS

As used herein, the term "halogen" (or halo) refers to fluorine, bromine, chlorine or iodine, in particular fluorine, chlorine.

As used herein, the term "alkyl" refers to a fully saturated branched or unbranched hydrocarbon moiety having up to 4 carbon atoms. Representative examples of alkyl include, but are not limited to, methyl, ethyl, n-propyl, iso-propyl, n-butyl, sec-butyl, iso-butyl, tert-butyl and the like.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, term-butoxy, pentyloxy, hexyloxy, cyclopropyloxy-, cyclohexyloxy- and the like. Typically, alkoxy groups have 1-4 carbon atoms.

As used herein, the term "cycloalkyl" refers to saturated or unsaturated monocyclic hydrocarbon groups of 3-6 carbon atoms, particularly 3-5 carbon atoms, especially 3-4 or 3 carbon atoms.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$, and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the invention, can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, e.g. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by protein kinase C, or (ii) associated with protein kinase C activity, or (iii) characterized by activity (normal or abnormal) of protein kinase C; or (2) reducing or inhibiting the activity of protein kinase C; or (3) reducing or inhibiting the expression of protein kinase C. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of protein kinase C; or at least partially reducing or inhibiting the expression of protein kinase C.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Methods of Manufacturing

The compounds of the invention may be manufactured by the methods provided below, e.g. by converting maleimide of formula (Va) into the alcohol of formula (Vb) for example with formaldehyde in the presence or absence of a solvent or a base such as potassium carbonate and optionally prior to this reaction by introducing protective groups, e.g. tert-butoxycarbonyl groups in accordance to the state-of-the-art reaction, for example when there are free and reactive amino-groups in a compound of formula (Va), wherein the variables, X, R, R1, R2, R3, R4 and R5 have the meanings as provided for formula (I).

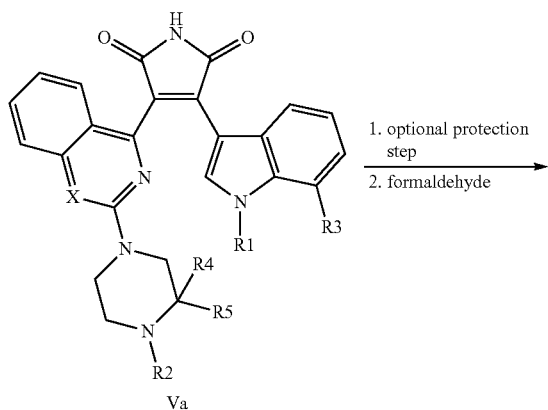

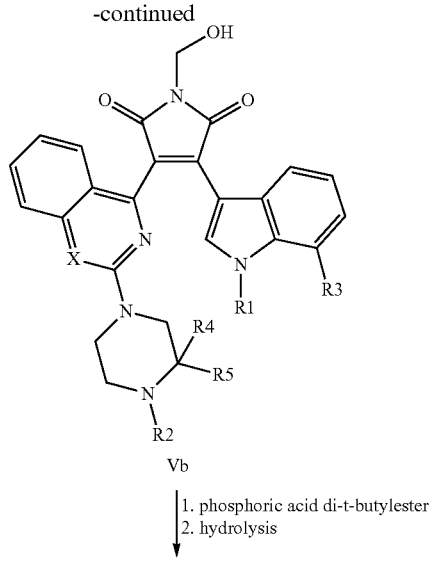

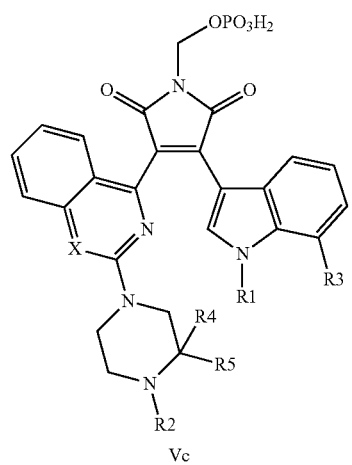

The alcohol of formula (Vb) may be optionally converted to a reactive ester, e.g. with trichloromethylacetonitril and and appropriate base, e.g. DBU, and may then be reacted with an appropriated phosphorylating agent, e.g. phosphoric acid di-tert-butylester in the presence or absence of an appropriate solvent, e.g. an aprotic solvent, e.g. acetonitril, and may then be hydrolysed, e.g. with trifluoroacetic acid e.g. in dicholoromethane or 1,2-dichloroethane to furnish the final product Vc.

Alternatively, the alcohol of formula (Vb) may be reacted directly with a phosphoric acid ester, e.g. with phosphoric acid di-tert-butylester, e.g. under Mitsunobu reaction conditions to furnish the phosphoric acid ester, which may then be hydrolised, e.g. with trifluoroacetic acid, e.g. in dichloromethane to furnish the final product Vc.

Experimental Part:

Insofar as the production of the starting materials is not particularly described, the compounds are known or may be prepared analogously to methods known in the art or as described hereafter.

The following examples are illustrative of the invention without any limitation.

ABBREVIATIONS bs broad singlet
d doublet
DMSO dimethylsulfoxide
d.n. dose normalized
EtOAc ethyl acetate
Et$_2$O diethyl ether
FCC flash column chromatography
MeOH methanol
MS mass spectroscopy
m multiplet
NMR nuclear magnetic resonance
p.o. per os
r.t. room temperature
s singulet
t triplet
TFA trifluoroacetic acid
TLC thin layer chromatography
UPLC ultra high pressure liquid chromatography The chemical nomenclature of all compounds was created by using AutoNom®.

NMR spectra were recorded on a Bruker Avance DPX 400 spectrometer at room temperature.

LCMS Methods Used:

LC Method 1 (Rt$^{(1)}$):

The retention times (Rt) were obtained on a Waters Acquity UPLC system linked to a Waters ZQ 2000 mass spectrometer using a Waters BEH C18 1.7 μm 2.1×50 mm column (flow rate=0.7 ml/min; detection 240-350 nm; DAD) applying a gradient (solvent A: water+0.1% formic acid, solvent B: acetonitrile; t=0 min: 99% A, 1% B; t=1 min 98% A, 2% B; t=2.25 min 1% A, 99% B; t=4.5 min 0% A, 100% B).

LC Method 2 (Rt$^{(2)}$):

The retention times (Rt) were obtained on a Agilent HPLC system with an Ascentis® Express column C18 2.7 μm, 30×2.1 mm (Supelco) applying a gradient (H$_2$O+0.05% formic acid+3.75 mM Ammonium acetate)/(CH$_3$CN+0.04% formic acid) 90/10 to 5/95 over 1.7 min and 1.2 mL/min as solvent flow and then 5/95 over 0.7 min with 1.4 mL/min as solvent flow and 40° C. for the oven temperature. Detection method UV 214-350 nm-MS.

Purification Method:

Preparative Reverse Phase Gilson HPLC

Column SunFire prep C18 OBD 5 μm, 30×100 mm from WATERS, with H$_2$O+0.1% TFA and Acetonitrile+0.1% TFA as mobile phase. Detection method UV 220-400 nm

Example 1

Phosphoric acid mono-[3-[3-(4,7-diaza-spiro[2.5]oct-7-yl)-isoquinolin-1-yl]-4-(7-methyl-1H-indol-3-yl)-2,5-dioxo-2,5-dihydro-pyrrol-1-ylmethyl]ester

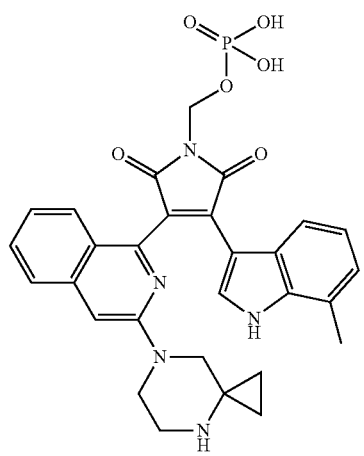 [SMILES: Cc1cccc2c(C3=C(c4nc(N5CCNC6(CC6)C5)cc5ccccc45)C(=O)N(COP(=O)(O)O)C3=O)c[nH]c12]

To a solution of 7-{1-[1-(di-tert-butoxy-phosphoryloxymethyl)-4-(7-methyl-1H-indol-3-yl)-2,5-dioxo-2,5-dihydro-1H-pyrrol-3-yl]-isoquinolin-3-yl}-4,7-diaza-spiro[2.5]octane-4-carboxylic acid tert-butyl ester (1.90 g, 2.42 mmol) in 1,2-dichloroethane (50 mL) was added TFA (8.27 g, 72.5 mmol) under argon at 0° C. The reaction mixture was stirred for 3.5 h under argon at 0° C. until UPLC-MS indicated that full conversion of the starting material had occurred. The reaction mixture was diluted with 1,2-dichloroethane (50 mL) and concentrated at reduced pressure to afford the crude product as a red solid. The crude reaction product was dissolved in MeOH and slowly concentrated at reduced pressure until crystallization started to occur. Pentane was added and the solids were filtered off and washed with Et$_2$O. Further purification was achieved by suspending the crude product in DMSO, followed by sonication for 30 min. The solids were filtered off, washed with Et$_2$O and dried at high vacuum (<1 mm Hg) to afford the title compound as a dark red solid. $^1$H-NMR (400 MHz, DMSO-d6): 12.10 (s, 1H), 8.08 (d, 1H), 7.65-7.61 (m, 2H), 7.44 (t, 1H), 7.20 (s, 1H), 7.06 (t, 1H), 6.74 (d, 1H), 6.43 (t, 1H), 6.00 (d, 1H), 5.29 (d, 2H), 3.87-3.01 (m, 6H), 2.37 (s, 3H), 0.97-0.62 (m, 4H). $^{31}$P-NMR (162 MHz, DMSO-d6): −6.0. LCMS: [M+1]$^+$=574.0, Rt$^{(1)}$=1.77 min., Rt$^{(2)}$=0.71 min.

Preparation of 7-{1-[4-(7-Methyl-1H-indol-3-yl)-2,5-dioxo-2,5-dihydro-1H-pyrrol-3-yl]-isoquinolin-3-yl}-4,7-diaza-spiro[2.5]octane-4-carboxylic acid tert-butyl ester

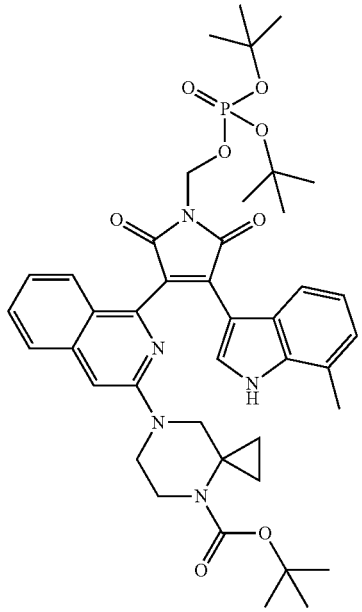 [SMILES: Cc1cccc2c(C3=C(c4nc(N5CCN(C(=O)OC(C)(C)C)C6(CC6)C5)cc5ccccc45)C(=O)N(COP(=O)(OC(C)(C)C)OC(C)(C)C)C3=O)c[nH]c12]

To a solution of 7-{1-[1-hydroxymethyl-4-(7-methyl-1H-indol-3-yl)-2,5-dioxo-2,5-dihydro-1H-pyrrol-3-yl]-isoquinolin-3-yl}-4,7-diaza-spiro[2.5]octane-4-carboxylic acid tert-butyl ester (7.30 g, 12.30 mmol) in acetonitrile (60 mL) was added dropwise a solution of DBU (0.374 g, 0.371 mL, 2.46 mmol) in trichloroacetonitrile (17.8 g, 12.3 mL, 123 mmol) at r.t. under argon. The reaction mixture was stirred for 5 h at r.t. until TLC (SiO$_2$, EtOAc/cyclohexane 6:4) indicated complete conversion. The reaction mixture was evaporated to dryness at reduced pressure and the residue was suspended in acetonitrile (60 mL). Phosphoric acid di-tert-butyl ester (3.36 g, 15.99 mmol) was added and the reaction mixture was stirred for approximately 3.5 h at r.t. under argon until TLC (SiO$_2$, EtOAc/cyclohexane 6:4) indicated that the reaction was complete. The reaction mixture was concentrated at reduced pressure and the residue was partitioned between EtOAc and water. The layers were separated and the organic phase was washed with water (5 times). The organic phase was dried over Na$_2$SO$_4$ and concentrated at reduced pressure to afford a red solid. The crude product was purified by FCC (Biotage SP4™ system, SiO$_2$, cyclohexane/EtOAc 20:80) to yield the title compound as a red solid. $^1$H-NMR (400 MHz, DMSO-d6): 12.03 (s, 1H), 8.08 (d, 1H), 7.70-7.65 (m, 2H), 7.47 (t, 1H), 7.11 (s, 1H), 7.11-7.07 (m, 1H), 6.77 (d, 1H), 6.44 (t, 1H), 5.97 (d, 1H), 5.39 (d, 1H), 3.49-3.08 (m, 6H), 2.39 (s, 3H), 1.45 (s, 18H), 1.41 (s, 9H), 0.87-0.56 (m, 4H). $^{31}$P-NMR (162 MHz, DMSO-d6): −12.1. LCMS: [M+1]$^+$=786.4, Rt$^{(1)}$=2.53 min., Rt$^{(2)}$=1.62 min.

Preparation of 7-{1-[1-Hydroxymethyl-4-(7-methyl-1H-indol-3-yl)-2,5-dioxo-2,5-dihydro-1H-pyrrol-3-yl]-isoquinolin-3-yl}-4,7-diaza-spiro[2.5]octane-4-carboxylic acid tert-butyl ester

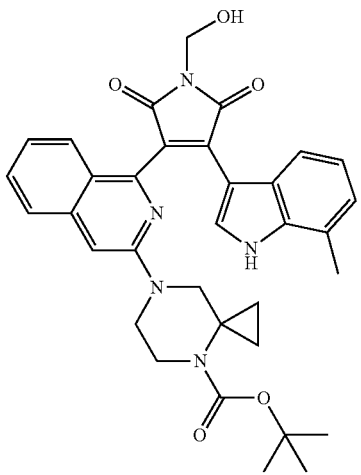 [SMILES: Cc1cccc2c(C3=C(c4nc(N5CCN(C(=O)OC(C)(C)C)C6(CC6)C5)cc5ccccc45)C(=O)N(CO)C3=O)c[nH]c12]

To a solution of 7-{1-[4-(7-methyl-1H-indol-3-yl)-2,5-dioxo-2,5-dihydro-1H-pyrrol-3-yl]-isoquinolin-3-yl}-4,7-diaza-spiro[2.5]octane-4-carboxylic acid tert-butyl ester (3.00 g, 5.32 mmol) in MeOH (25 mL) was added an aqueous 37% solution of formaldehyde (9.5 g, 8.72 mL, 117 mmol) under argon at r.t. The reaction mixture was heated to 85° C. and stirred for 4 h. The reaction mixture was cooled to r.t. under continuous stirring and filtered. The solids were washed with ice-water and dried at high vacuum (<1 mm Hg) to afford the title compound as dark red crystals. $^1$H-NMR (400 MHz, DMSO-d6): 11.96 (s, 1H), 8.05 (s, 1H), 7.69-7.64 (m, 2H), 7.47 (t, 1H), 7.12-7.06 (m, 2H), 6.76 (d, 1H), 6.42 (t, 1H), 6.01 (d, 1H), 5.00 (d, 2H), 3.49-3.10 (m, 6H), 2.39 (s, 3H), 1.41 (s, 9H), 0.89-0.57 (m, 4H). LCMS: [M]$^+$=593.7, Rt$^{(1)}$=2.34 min.

Preparation of 7-{1-[4-(7-Methyl-1H-indol-3-yl)-2,5-dioxo-2,5-dihydro-1H-pyrrol-3-yl]-isoquinolin-3-yl}-4,7-diaza-spiro[2.5]octane-4-carboxylic acid tert-butyl ester

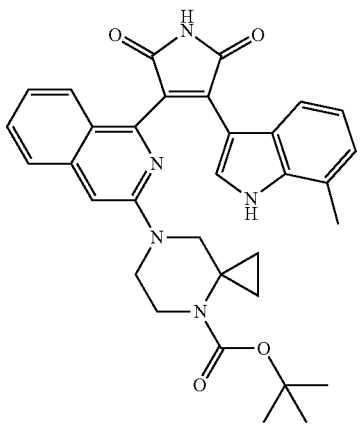 [SMILES: Cc1cccc2c(C3=C(c4nc(N5CCN(C(=O)OC(C)(C)C)C6(CC6)C5)cc5ccccc45)C(=O)NC3=O)c[nH]c12]

Di-tert-butyl dicarbonate (2.77 g, 10.8 mmol) and triethylamine (2.18 g, 21.6 mmol) were added to a solution of 3-[3-(4,7-diaza-spiro[2.5]oct-7-yl)-isoquinolin-1-yl]-4-(7-methyl-1H-indol-3-yl)-pyrrole-2,5-dione (5.0 g, 10.8 mmol) in THF (50 mL) under argon at r.t. The reaction mixture was stirred for 16 h and concentrated at reduced pressure. The residue was partitioned between a saturated aqueous NH$_4$Cl solution and CH$_2$Cl$_2$. The layers were partitioned and the aqueous layer was extracted with CH$_2$Cl$_2$. The combined organic layers were washed with a saturated aqueous NaHCO$_3$ solution and brine, dried over anhydrous Na$_2$SO$_4$ and concentrated at reduced pressure to afford the title compound as an orange solid. $^1$H-NMR (400 MHz, DMSO-d6): 11.88 (s, 1H), 11.15 (s, 1H), 8.00 (d, 1H), 7.68-7.65 (m, 2H), 7.46 (t, 1H), 7.09 (t, 1H), 7.06 (s, 1H), 6.73 (d, 1H), 6.41 (t, 1H), 6.01 (d, 1H), 3.48-3.16 (m, 6H), 2.38 (s, 3H), 1.40 (s, 9H), 0.87-0.54 (m, 4H). LCMS: [M+1]$^+$=563.9, Rt$^{(1)}$=3.51 min, Rt$^{(1)}$=2.36 min., Rt$^{(2)}$=1.37 min.

Example 2

3-[3-(4,7-Diaza-spiro[2.5]oct-7-yl)-isoquinolin-1-yl]-1-hydroxymethyl-4-(7-methyl-1H-indol-3-yl)-pyrrole-2,5-dione

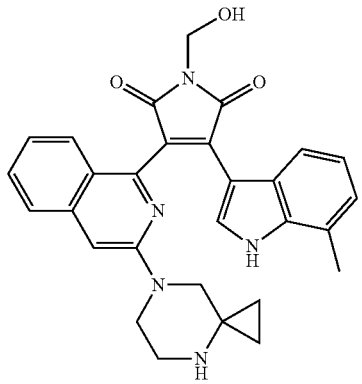 [SMILES: Cc1cccc2c(C3=C(c4nc(N5CCNC6(CC6)C5)cc5ccccc45)C(=O)N(CO)C3=O)c[nH]c12]

To a solution of 7-{1-[1-hydroxymethyl-4-(7-methyl-1H-indol-3-yl)-2,5-dioxo-2,5-dihydro-1H-pyrrol-3-yl]-isoquinolin-3-yl}-4,7-diaza-spiro[2.5]octane-4-carboxylic acid tert-butyl ester (500 mg, 0.842 mmol) in 1,2-dichloroethane (5 mL) was added TFA (1.44 g, 0.973 mL, 12.7 mmol) under argon at 0° C. The reaction mixture was stirred for 1 h under argon at 0° C. after which additional TFA (0.768 g, 0.52 mL, 6.74 mmol) was added. Stirring was continued for 1.5 h at 0° C. The reaction mixture was evaporated to dryness at reduced pressure and the crude product was crystallised from MeOH to afford the title compound as a red solid (TFA salt) as a dark red solid. $^1$H-NMR (400 MHz, DMSO-d6): 12.01 (d, 1H), 9.06 (bs, 2H), 8.11 (d, 1H), 7.71-7.66 (m, 2H), 7.51 (t, 1H), 7.27 (s, 1H), 7.14 (t, 1H), 6.77 (d, 1H), 6.45-6.39 (m, 2H), 5.92 (d, 1H), 5.00 (d, 2H), 3.84-3.54 (m, 6H), 2.39 (s, 3H), 0.96-0.67 (m, 4H). LCMS: [M+1]$^+$=493.7, Rt$^{(1)}$=1.84 min.

Example 3

3-[3-(4,7-diaza-spiro[2.5]oct-7-yl)-isoquinolin-1-yl]-4-(7-methyl-1H-indol-3-yl)-pyrrole-2,5-dione

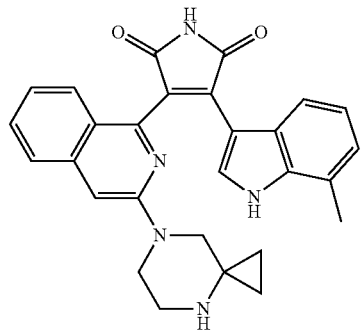 [SMILES: Cc1cccc2c(C3=C(c4nc(N5CCNC6(CC6)C5)cc5ccccc45)C(=O)NC3=O)c[nH]c12]

The synthesis of the title compound has been described as Example 69 in WO03082859.

Example 4

Phosphoric acid mono-{3-(1H-indol-3-yl)-4-[2-(4-methyl-piperazin-1-yl)-quinazolin-4-yl]-2,5-dioxo-2,5-dihydro-pyrrol-1-ylmethyl}ester

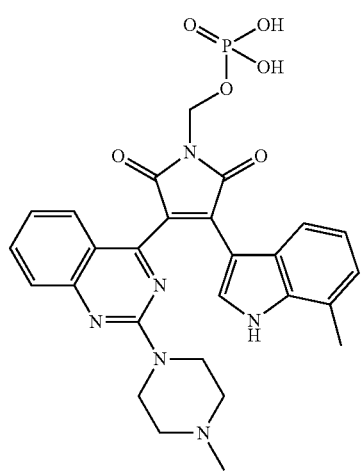 [SMILES: Cc1cccc2c(C3=C(c4nc(N5CCN(C)CC5)nc5ccccc45)C(=O)N(COP(=O)(O)O)C3=O)c[nH]c12]

Under argon, phosphoric acid di-tert-butyl ester chloromethyl ester (1.24 g, 4.81 mmol) and $Cs_2CO_3$ (3.14 g, 9.63 mmol) were added to a solution of 3-(1H-indol-3-yl)-4-[2-(4-methyl-piperazin-1-yl)-quinazolin-4-yl]-pyrrole-2,5-dione (2.0 g, 4.01 mmol) in acetone (40 mL). The reaction mixture was stirred under argon for 16 h at 50° C. followed by concentration at reduced pressure. The residue was partitioned between EtOAc and a saturated aqueous $NH_4Cl$ solution, the layers were separated and the organic layer was dried over anhydrous $Na_2SO_4$. Concentration at reduced pressure afforded the crude product as a red foam. The crude product was purified by reverse phase Gilson HPLC as described above. After concentration of the desired fractions in vacuo, a red solid was obtained. UPLC-MS indicated that partial cleavage of the t-butyl ester groups had occurred. The thus obtained mixture (280 mg) was dissolved in a mixture of 1,2-dichloroethane (4 mL) and acetonitrile (2.0 mL). TFA (145 mg, 98 µL, 1.27 mmol) was added and the resulting solution was stirred for 3 h under argon at 0° C. when UPLC-MS indicated that full conversion of the starting material had occurred. The reaction mixture was diluted with 1,2-dichloroethane (4.0 mL) and concentrated at reduced pressure to afford the crude product as a red solid. The crude reaction product was dissolved in MeOH (3 mL) and slowly concentrated at reduced pressure until crystallization started to occur. The crystals were filtered off and washed with $Et_2O$ and pentane to afford the title compound as an orange solid.
$^1$H-NMR (400 MHz, DMSO-d6): 12.27 (s, 1H), 8.21 (s, 1H), 7.72-7.66 (m, 2H), 7.58 (d, 1H), 7.40 (d, 1H), 7.14 (t, 1H), 7.02 (t, 1H), 6.65 (t, 1H), 6.24 (d, 1H), 5.34 (d, 2H), 4.14-3.72 (bs, 4H), 3.00-2.73 (bs, 4H), 2.60 (s, 3H). $^{31}$P-NMR (162 MHz, DMSO-d6): −2.7. LCMS: [M]$^+$=548.6, Rt$^{(1)}$=1.72 min., Rt$^{(2)}$=0.73 min.

Preparation of Crystalline Material of the Compound of Example 1:

2 grams of phosphoric acid mono-[3-[3-(4,7-diaza-spiro[2.5]oct-7-yl)-isoquinolin-1-yl]-4-(7-methyl-1H-indol-3-yl)-2,5-dioxo-2,5-dihydro-pyrrol-1-ylmethyl]ester (example No. 1) were dispersed in a mixture of 800 ml ethanol and 200 ml of water. This suspension was stirred at room temperature for 3 days. Thereafter, said suspension was filtered through a sintered glass filter and the crystals so obtained were dried in normal atmospheric air stream. To 1 gram of these crystals, 4 ml of a solution of 80% ethanol/20% water (vol./vol.) was added and the resulting mixture was evaporated to dryness at atmospheric pressure to furnish the mono-hydrate of example No. 1.

FIG. 1

An X-ray diffractogram of the above crystalline monohydrate is shown in FIG. 1, and peaks are recorded against the angle 2 theta in table 1.

TABLE 1

Main peaks on the X-Ray diffraction pattern of the crystalline mono-hydrate of example No. 1

| Angle 2θ | d value Angstrom | Intensity Counts | Count % | Intensity | Intensity % |
|---|---|---|---|---|---|
| 8.506 | 10.38645 | 8.506 | 10.38645 | 5215 | 26.0 |
| 9.525 | 9.27790 | 9.525 | 9.27790 | 7052 | 35.2 |
| 13.793 | 6.41501 | 13.793 | 6.41501 | 4245 | 21.2 |
| 14.926 | 5.93044 | 14.926 | 5.93044 | 3513 | 17.5 |
| 15.172 | 5.83502 | 15.172 | 5.83502 | 3360 | 16.8 |
| 15.413 | 5.74440 | 15.413 | 5.74440 | 3384 | 16.9 |
| 16.356 | 5.41519 | 16.356 | 5.41519 | 6738 | 33.6 |
| 17.091 | 5.18400 | 17.091 | 5.18400 | 20046 | 100 |
| 18.005 | 4.92268 | 18.005 | 4.92268 | 10587 | 52.8 |
| 19.224 | 4.61338 | 19.224 | 4.61338 | 6442 | 32.1 |
| 20.859 | 4.25526 | 20.859 | 4.25526 | 9742 | 48.6 |
| 22.433 | 3.96009 | 22.433 | 3.96009 | 5332 | 26.6 |
| 23.316 | 3.81209 | 23.316 | 3.81209 | 5751 | 28.7 |
| 25.792 | 3.45140 | 25.792 | 3.45140 | 8574 | 42.8 |
| 27.402 | 3.25222 | 27.402 | 3.25222 | 3930 | 19.6 |
| 27.712 | 3.21657 | 27.712 | 3.21657 | 3575 | 17.8 |
| 28.091 | 3.17398 | 28.091 | 3.17398 | 4187 | 20.9 |
| 30.521 | 2.92662 | 30.521 | 2.92662 | 2899 | 14.5 |
| 31.502 | 2.83768 | 31.502 | 2.83768 | 3756 | 18.7 |

Accordingly, the present invention provides in another embodiment a crystalline form of phosphoric acid mono-[3-[3-(4,7-diaza-spiro[2.5]oct-7-yl)-isoquinolin-1-yl]-4-(7-methyl-1H-indol-3-yl)-2,5-dioxo-2,5-dihydro-pyrrol-1-ylmethyl]ester, especially the mono-hydrate, which preferably has an X-ray powder diffraction pattern with at least one, preferably two, more preferably three, even more preferably four, especially five, most preferably all of the following peaks at an angle of refraction 2 theta (θ) of 9.525, 16.356, 17.091, 18.005, 20.859, each ±0.2, especially as depicted in FIG. 1.

TABLE 2

Chemical stability of amorphous and crystalline example No. 1

| Compound | Solid State | Initial Purity (%) | Temperature [° C.] | Exposure Time | Purity [%] |
|---|---|---|---|---|---|
| Example No. 1 | Amorphous | 98.5 | 50 | 1 week | 95.8 |
| Example No. 1 | Amorphous | 98.5 | 80 | 1 week | 89.7 |
| Example No. 1 | Crystalline mono-hydrate | 100 | 50 | 1 week | 100 |
| Example No. 1 | Crystalline mono-hydrate | 100 | 80 | 1 week | 100 |

Table summarizing the thermal events seen on DSC (differential scanning calorimetry) and TGA (thermal gravimetric analysis)

| Temperature range [° C.] | Event |
|---|---|
| 30-125 | Loss of water |
| 225-265 | Degradation |

FIG. 2

Figure 2:
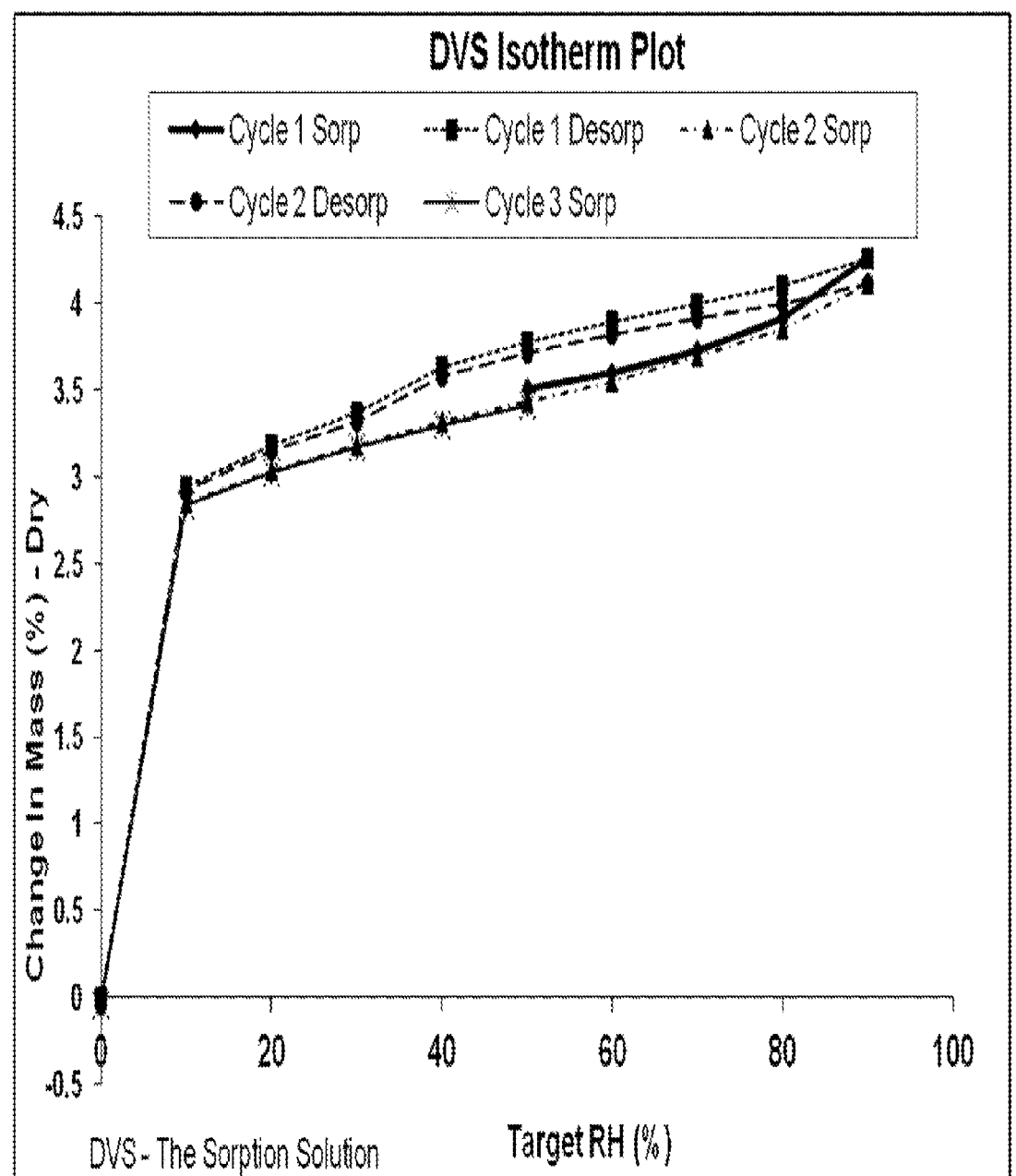
FIG. 2 shows the water absorption profile of crystalline Example No. 1 mono-hydrate [6 h equilibration at 50% RH, followed by 2 RH cycles from 50% RH to 90% RH to 0% RH to 90% RH to 0% RH to 50% RH in 10% RH steps]. RH=Relative Humidity.

The water sorption profile of the crystalline Example No. 1 mono-hydrate is shown in FIG. 2. The following humidity exposure is applied: 6 h equilibration at 50% RH, followed by 2 RH cycles from 50% RH to 90% RH to 0% RH to 90% RH to 0% RH to 50% RH in 10% RH steps. (RH=relative humidity)

Biopharmaceutical Part

The compounds of the invention, for example a compound of formulae (I), (II), (III) or (IV) and the like in free form or in pharmaceutically acceptable salt or hydrate form, exhibit valuable pharmacological properties as described in the tests below, e.g. in vitro and in vivo tests, and are therefore indicated for therapy.

A. In vitro
1. Protein Kinase C Alpha and Theta Assays

The compounds of the invention were tested for their activity on different PKC isotypes according to the following method. All assays were performed in 384 well microtiter plates. Each assay plate contained 8-point serial dilutions for 40 test compounds, as well as two 16-point serial dilutions of staurosporine as reference compound, plus 16 high- and 16 low controls. Liquid handling and incubation steps were done on a automated workstation equipped with a Innovadyne Nanodrop Express.

The assay plates were prepared by addition of 50 nL per well of compound solution in 90% DMSO. The kinase reactions were started by stepwise addition of 4.5 µl per well of a 2× peptide/ATP-solution and 4.5 µl per well of a 2× enzyme solution. The final concentration of reagents during kinase reaction were: 50 mM HEPES, pH 7.5, 1 mM DTT, 0.02% Tween20, 0.02% BSA, 0.6% DMSO, 10 mM beta-glycerophosphate, and 10 µM sodium orthovanadate. The peptide substrate used in the PKC-alpha and PKC-theta assays was Dy495-X5-ME-Mpr-RFARKGSLRQKNV-COOH. Both enzymes were full length human recombinant protein expressed in insect cells (Invitrogen AG, Basel, Switzerland).

Other components were adjusted specifically for the respective kinase assays: PKC-alpha: 12 pM enzyme, 17 µM ATP, 1 µM peptide substrate, 7 mM $MgCl_2$, 0.2 mM $CaCl_2$. PKC-theta: 29 pM enzyme, 70 µM ATP, 1 µM peptide substrate, 7 mM $MgCl_2$, 0.2 mM $CaCl_2$.

Kinase reactions were incubated at 30° C. for 60 minutes and subsequently terminated by addition of 16 µl per well of stop solution (100 mM HEPES pH 7.5, 5% DMSO, 0.1% Caliper coating reagent, 10 mM EDTA, and 0.015% Brij35).

Plates with terminated kinase reactions were transferred to the Caliper LC3000 workstations for reading. Phosphorylated and unphosphorylated peptides were separated using the Caliper microfluidic mobility shift technology and Kinase activities were calculated from the amounts of formed phospho-peptide.

| Assay | Example 1 | Example 3 |
|---|---|---|
| PKCα ($IC_{50}$ in nM) | 1677 | 0.4 |
| PKCθ ($IC_{50}$ in nM) | 462 | 0.2 |

Test results shown herein above and herein below may support the prodrug concept of the compounds of the invention.

2. Bone Marrow Cell Proliferation (BM) Assay

Bone marrow cells from CBA mice ($2.5 \times 10^4$ cells per well in flat bottom tissue culture microtiter plates) were incubated in 100 µL RPMI medium containing 10% FCS, 100 U/mL penicillin, 100 µg/mL streptomycin (Gibco BRL, Basel Switzerland), 50 µM 2-mercaptoethanol (Fluka, Buchs, Switzerland), WEHI-3 conditioned medium (7.5% v/v) and L929 conditioned medium (3% v/v) as a source of growth factors and serially diluted compounds. Seven three-fold dilution steps in duplicates per test compounds were performed. After four days of incubation 1 µCi $^3$H-thymidine was added. Cells were harvested after an additional five-hour incubation period, and incorporated $^3$H-thymidine was determined according to standard procedures. Conditioned media were prepared as follows. WEHI-3 cells (ATCC TIB68) and L929 cells (ATCC CCL 1) were grown in RPMI medium until confluence for 4 days and one week, respectively. Cells were harvested, resuspended in the same culture flasks in medium C containing 1% FCS (Schreier and Tess 1981) for WEHI-3 cells and RPMI medium for L929 cells and incubated for 2 days (\NEHI-3) or one week (L929). The supernatant was collected, filtered through 0.2 µm and stored in aliquots at −80° C. Cultures without test compounds and without WEHI-3 and L929 supernatants were used as low control values. Low control values were subtracted from all values. High controls without any sample were taken as 100% proliferation. Percent inhibition by the samples was calculated and the concentrations required for 50% inhibition ($IC_{50}$ values) were determined.

| | Example 1 | Example 3 |
|---|---|---|
| $IC_{50}$ in nM | 6741 ± 1117 | 1672 ± 256 |

B. In vivo:
Administration of Compound of Example No. 1

A single dose of the compound of example 1 (3.0 mg/kg) was administered p.o. to 3 male Beagle dogs. Compound 1 was dosed as an aqueous suspension of the crystalline monohydrate form in Methylcellulose (0.5%): Tween 80 (1%) (90:

10). Blood was taken in regular intervals by venipuncture, and the samples were analyzed for a period of up to 24 hours. The compounds of the examples 1, 2, and 3 were quantitatively assessed over time, and the results are tabulated below:

| Time (h) | Compound 1 (nM) | Compound 2 (nM) | Compound 3 (nM) |
|---|---|---|---|
| 0 | — | — | — |
| 0.083 | — | 10.0 | 15.0 |
| 0.25 | 3.1 | 39.6 | 166.7 |
| 0.5 | 1.1 | 31.3 | 757.4 |
| 0.75 | — | 19.1 | 1198.0 |
| 1 | — | 6.3 | 1308.3 |
| 2 | — | 7.7 | 1118.6 |
| 3 | — | 1.0 | 958.9 |
| 4 | — | — | 762.0 |
| 7 | — | — | 403.1 |
| 24 | — | — | 67.9 |

Key pharmacokinetic parameters (mean values±standard deviations (n=3) for 1, 2 and 3 after oral dosing of example No. 1.

| Parameters | Compound 1 | Compound 2 | Compound 3 |
|---|---|---|---|
| $C_{max}$ d.n. (nM) | — | 15 ± 8 | 441 ± 165 |
| $T_{max}$ (h) | — | 0.4 ± 0.1 | 0.9 ± 0.1 |
| AUC d.n. (nM · h) | — | low | 3350 ± 1402 |

Administration of Compound of Example No. 3

Compound of Example No. 3 was administered orally as the mono acetate salt in a hard gelatine capsule to 6 fasted male Beagle dogs. A nominal dose of 100 mg/dog was given, resulting in dose of 8.9-11.3 mg/kg (weight of the dogs ranging from 8.9-11.3 kg). Blood was taken by venipuncture, and sampling was performed up to 32 h. Bioanalytic determination was performed for 3 and is tabulated below:

| Time (h) | Compound 3 (nM) |
|---|---|
| 0 | — |
| 0.25 | 177 |
| 0.5 | 936 |
| 1 | 2155 |
| 2 | 2548 |
| 3 | 2000 |
| 4 | 1898 |
| 6 | 1486 |
| 8 | 1238 |
| 24 | 276 |
| 32 | 116 |

Key pharmacokinetic parameters (mean values or range) for compound No. 3 after oral dosing as described above.

| Parameters | Compound 3 |
|---|---|
| $C_{max}$ d.n. (nM) | 323 |
| $T_{max}$ (h) | 0.5-2 |
| AUC d.n. (nM · h) | 2790 |

Physicochemical Section
Solubility Assessments

Solubility of compound Example No. 1 in simulated gastric and in simulated intestinal fluids at room temperature

| Media | Solubility [mg/mL] | Final pH |
|---|---|---|
| Simulated gastric fluid (SGF) pH 2 | 0.04 | 2.22 |
| Fasted state simulated intestinal fluid (FaSSIF) pH 6.5 | 0.1 | 6.59 |
| Fed state simulated intestinal fluid (FeSSIF) pH 5.8 | 0.13 | 6.05 |

Solubility of compound Example No. 3 (free form/acetate salt form) in simulated gastric fluids:

| | Free Form | | Acetate Salt | |
|---|---|---|---|---|
| Media | Solubility [mg/ml] | Final pH | Solubility [mg/ml] | Final pH |
| Simulated gastric fluid (SGF) pH 2 | 0.12 | — | 0.15 | 5.45 |
| Fasted state simulated intestinal fluid (FaSSIF) pH 6.5 | 0.03 | — | 0.05 | 3.97 |
| Fed state simulated intestinal fluid (FeSSIF) pH 5.8 | 0.28 | — | 0.55 | 6.5 |

Stability Assessments
Stability of Cpd. Example No. 1 in Gastric and Intestinal Simulated Fluids at 37° C.:

| Media | Time (hours) | Amount in Area % of compound example No. 1 |
|---|---|---|
| Simulated gastric fluid (SGF) pH 2 | 0 | 95.9 |
| | 1 | 95.5 |
| | 2.5 | 95.3 |
| | 4.2 | 95.6 |
| | 7 | 95.6 |
| Fasted state simulated intestinal fluid (FaSSIF) pH 6.5 | 0 | 95.1 |
| | 1 | 93.8 |
| | 2.5 | 92.3 |
| | 4.2 | 90.5 |
| | 7 | 87.7 |
| Fed state simulated intestinal fluid (FeSSIF) pH 5.8 | 0 | 95.0 |
| | 1 | 94.9 |
| | 2.5 | 94.8 |
| | 4.2 | 94.8 |
| | 7 | 94.8 |

Stability of compound Example No. 3
(Free form/acetate salt form) in gastric and intestinal simulated fluids at 37° C.:

| Media | Time (hours) | Free Form Amount in Area % of compound example No. 3 | Acetate Salt Amount in Area % of compound example No. 3 |
|---|---|---|---|
| Simulated gastric fluid (SGF) pH 2 | 0 | 98.8 | 100 |
| | 1 | 98.6 | 96.4 |
| | 2.5 | 98.1 | 93.2 |
| | 4 | 97.9 | 92.4 |
| | 7 | 97.9 | 90.0 |
| Fasted state simulated intestinal fluid (FaSSIF) pH 6.5 | 0 | 100 | 100 |
| | 1 | 100 | 98.6 |
| | 2.5 | 100 | 98.7 |
| | 4 | 90.7 | 95.1 |
| | 7 | 82.5 | 88.5 |
| Fed state simulated intestinal fluid | 0 | 100 | 100 |
| | 1 | 100 | 99.1 |

| Media | Time (hours) | Free Form Amount in Area % of compound example No. 3 | Acetate Salt Amount in Area % of compound example No. 3 |
|---|---|---|---|
| (FeSSIF) pH 5.8 | 2.5 | 100 | 98.9 |
| | 4 | 99.2 | 98 |
| | 7 | 98.7 | 97.5 |

Utility Section

The compounds of the present invention are typically useful in the prevention or treatment of disorders or diseases where PKC, or mediators of other kinases play a role, for example in diseases or disorders mediated by T lymphocytes, B lymphocytes, mast cells, eosinophils or cardiomyocytes, and hence are typically indicated in acute or chronic rejection of organ or tissue allo- or xenografts, graft-versus-host disease, host-versus-graft disease, atheriosclerosis, cerebral infarction, vascular occlusion due to vascular injury such as angioplasty, restenosis, fibrosis (especially pulmonary, but also other types of fibrosis, such as renal fibrosis), angiogenesis, hypertension, heart failure, chronic obstructive pulmonary disease, CNS disease such as Alzheimer disease or amyotrophic lateral sclerosis, cancer, infectious disease such as AIDS, septic shock or adult respiratory distress syndrome, ischemia/reperfusion injury e.g. myocardial infarction, stroke, gut ischemia, renal failure or hermorrhage shock, or traumatic shock.

The compounds of the invention are also useful in the treatment and/or prevention of acute or chronic inflammatory diseases or disorders or autoimmune diseases e.g. sarcoidosis, fibroid lung, idiopathic interstitial pneumonia, obstructive airways disease, including conditions such as asthma, intrinsic asthma, extrinsic asthma, dust asthma, particularly chronic or inveterate asthma (for example late asthma and airway hyperreponsiveness), bronchitis, including bron-chial asthma, infantile asthma, rheumatoid arthritis, osteoarthritis, systemic lupus erythematosus, nephrotic syndrome lupus, Hashimoto's thyroiditis, multiple sclerosis, myasthenia gravis, type I diabetes mellitus and complications associated therewith, type II adult onset diabetes mellitus, uveitis, nephrotic syndrome, steroid dependent and steroid-resistant nephrosis, palmoplantar pustulosis, allergic encephalomyelitis, glomerulonephritis, psoriasis, psoriatic arthritis, atopic eczema (atopic dermatitis), allergic contact dermatitis, irritant contact dermatitis and further eczematous dermatitises, seborrheic dermatitis, lichen planus, pemphigus, bullous pemphigoid, epidermolysis bullosa, urticaria, angioedemas, vas-culitides, erythemas, cutaneous eosinophilias, acne, alopecia areata, eosinophilic fasciitis, atherosclerosis, conjunctivitis, keratoconjunctivitis, keratitis, vernal conjunctivitis, uveitis associated with Behcet's disease, herpetic keratitis, conical cornea, Sjoegren's syndrome, dystorphia epithelialis corneae, keratoleukoma, ocular pemphigus, Mooren's ulcer, scleritis, Graves' ophthalmopathy, severe intraocular inflammation, inflammation of mucosa or blood vessels such as leukotriene B4-mediated diseases, gastric ulcers, vascular damage caused by ischemic diseases and thrombosis, cardiac hypertrophy, ischemic bowel disease, inflammatory bowel disease (e.g. Crohn's disease or ulcerative colitis), necrotizing enterocolitis, renal diseases including interstitial nephritis, Goodpasture's syndrome hemolytic uremic syndrome and diabetic nephropathy, nervous diseases selected from multiple myositis, Guillain-Barre syndrome, Meniere's disease and radiculopathy, collagen disease including scleroderma, Wegener's granuloma and Sjogren' syndrome, chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), cirrhosis, fulminant hepatitis, pustular psoriasis, Behcet's disease, active chronic hepatitis, Evans syndrome, pollinosis, idiopathic hypoparathyroidism, Addison disease, autoimmune atrophic gastritis, lupoid hepatitis, tubulointerstitial nephritis, membranous nephritis, or rheumatic fever.

The compounds of the invention may also be useful for treating tumors, e.g. breast cancer, genitourinary cancer, lung cancer, gastrointestinal cancer, epidermoid cancer, melanoma, ovarian cancer, pancreas cancer, neuroblastoma, head and/or neck cancer or bladder cancer, or in a broader sense renal, brain or gastric cancer; in particular (i) a breast tumor; an epidermoid tumor, such as an epidermoid head and/or neck tumor or a mouth tumor; a lung tumor, for example a small cell or non-small cell lung tumor; a gastrointestinal tumor, for example, a colorectal tumor; or a genitourinary tumor, for example, a prostate tumor (especially a hormone-refractory prostate tumor); or (ii) a proliferative disease that is refractory to the treatment with other chemotherapeutics; or (iii) a tumor that is refractory to treatment with other chemotherapeutics due to multidrug resistance.

The compounds may also useful for treating tumors of blood and lymphatic system (e.g. Hodgkin's disease, Non-Hodgkin's lymphoma, Burkitt's lymphoma, AIDS-related lymphomas, malignant immunoproliferative diseases, multiple myeloma and malignant plasma cell neoplasms, lymphoid leukemia, acute or chronic myeloid leukemia, acute or chronic lymphocytic leukemia, monocytic leukemia, other leukemias of specified cell type, leukemia of unspecified cell type, other and unspecified malignant neoplasms of lymphoid, haematopoietic and related tissues, for example diffuse large cell lymphoma, T-cell lymphoma or cutaneous T-cell lymphoma). Myeloid cancer includes e.g. acute or chronic myeloid leukaemia.

Where a tumor, a tumor disease, a carcinoma or a cancer are mentioned, also metastasis in the original organ or tissue and/or in any other location are implied alternatively or in addition, whatever the location of the tumor and/or metastasis.

Preferably the compounds of the present invention are in particular useful in the prevention and/or treatment of a disease or a disorder mediated by T lymphocytes such as acute or chronic rejection of organ or tissue allo- or xenografts, graft-versus-host disease, host-versus-graft disease, multiple sclerosis, psoriasis, or rheumatoid arthritis.

Poor bioavailability of drug products is very often a limiting factor for pharmaceutically effective ingredients. Moreover bioavailability might be species dependent. For example a well absorbed drug in mice, rat or dog or the like may not translate into a proper bioavailability in men. The present invention addresses this problem by providing a prodrug compound of formula (I) producing a favorable bioavailability for its parent compounds, in particular in men. For example, as shown in the experimental section, the compound of example 1 is converted into compound of example 3 which can be detected in the blood as the main component shortly after administration (for example after around an hour), and hence demonstrates the effective and favorable conversion into the parent compound.

For the above uses the required dosage will of course vary depending on the mode of administration, the particular condition to be treated and the effect desired. In general, satisfactory results are indicated to be obtained systemically at daily dosages of from about 0.02 to 25 mg/kg per body weight. An indicated daily dosage in the larger mammal, e.g. humans, may be typically in the range from about 0.2 mg to about 2 g, conveniently administered, for example, in divided doses up to four times a day or in retard form. Suitable unit dosage forms for oral administration may typically comprise from ca. 0.1 to 500 mg active ingredient.

The compounds of the invention may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration may for example be to the skin. A further form of topical administration may be to the eye. Pharmaceutical compositions comprising a compound of the invention in association with at least one pharmaceutical acceptable carrier or diluent may be manufactured in conventional manner by mixing with a pharmaceutically acceptable carrier or diluent.

The compounds of the invention may be administered in free form or in pharmaceutically acceptable salt form or in hydrate form, e.g. as indicated above. Such salts or hydrates may be prepared in conventional manner and may typically exhibit the same order of activity as the free compounds.

In accordance with the foregoing, the present invention also provides:
(1) A compound of the invention or a pharmaceutically acceptable salt or hydrate thereof, for use as a pharmaceutical;
(2) A compound of the invention or a pharmaceutically acceptable salt or hydrate thereof, for use as a PKC inhibitor, for example for use in any of the particular indications hereinbefore set forth;
(3) A pharmaceutical composition, e.g. for use in any of the indications herein before set forth, comprising a compound of the invention or a pharmaceutically acceptable salt or hydrate thereof, together with one or more pharmaceutically acceptable diluents or carriers therefor;
(4) A method for the treatment or prevention of a disease or condition in which PKC activation plays a role or is implicated, e.g. for the treatment of any of particular indication hereinbefore set forth in a subject in need thereof which comprises administering to the subject an effective amount of a compound of the invention or a pharmaceutically acceptable salt or hydrate thereof;
(5) The use of a compound of the invention or a pharmaceutically acceptable salt or hydrate thereof, for the manufacture of a medicament for the treatment or prevention of a disease or condition in which PKC activation plays a role or is implicated; e.g. as indicated above.

Combinations

The compounds of the invention may be administered as the sole active ingredient or in conjunction with, e.g. as an adjuvant to, other drugs e.g. in immunosuppressive or immunomodulating regimens or other anti-inflammatory agents, e.g. for the treatment or prevention of allo- or xenograft acute or chronic rejection or inflammatory or autoimmune disorders, a chemotherapeutic agent or an anti-infective agent, e.g. an anti-viral agent such as e.g. an anti-retroviral agent or an antibiotic.

For example, the compounds of the invention may be used in combination with a calcineurin inhibitor, e.g. cyclosporin A, ISA247 or FK 506; a mTOR inhibitor, e.g. rapamycin, 40-O-(2-hydroxyethyl)-rapamycin, CC1779, ABT578, TAFA-93, AP23573, AP23464, AP23841, biolimus-7 or biolimus-9; an ascomycin having immuno-suppressive properties, e.g. ABT-281, ASM981, etc.; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a SIP receptor agonist or modulator, e.g. FTY720 optionally phosphorylated or an analog thereof, e.g. 2-amino-2-[4-(3-benzyloxyphenylthio)-2-chlorophenyl]ethyl-1,3-propanediol optionally phosphorylated or 1-{4-[1-(4-cyclohexyl-3-trifluoromethyl-benzylmimino)-ethyl]-2-ethyl-benzyl}-azetidine-3-carboxylic acid or its pharmaceutically acceptable salts; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists, e.g. natalizumab (ANTEGREN®); or antichennokine antibodies or antichemokine receptor antibodies, or low molecular weight chemokine receptor antagonists, e.g. anti MCP-1 antibodies.

A compound of the invention may also be used in combination with other antiproliferative agents. Such antiproliferative agents include, but are not limited to:
(i) aromatase inhibitors, e.g. steroids, especially exemestane and formestane and, in particular, non-steroids, especially aminoglutethimide, vorozole, fadrozole, anastrozole and, very especially, letrozole;
(ii) antiestrogens, e.g. tamoxifen, fulvestrant, raloxifene and raloxifene hydrochloride;
(iii) topoisomerase I inhibitors, e.g. topotecan, irinotecan, 9-nitrocamptothecin and the macromolecular camptothecin conjugate PNU-166148 (compound A1 in WO99/17804);
(iv) topoisomerase II inhibitors, e.g. the antracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide;
(v) microtubule active agents, e.g. the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D;
(vi) alkylating agents, e.g. cyclophosphamide, ifosfamide and melphalan;
(vii) histone deacetylase inhibitors;
(viii) farnesyl transferase inhibitors;
(ix) COX-2 inhibitors, e.g. celecoxib (Celebrex®), rofecoxib (Vioxx®) and lumiracoxib (COX189);
(x) MMP inhibitors;
(xi) mTOR inhibitors;
(xii) antineoplastic antimetabolites, e.g. 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719;

(xiii) platin compounds, e.g. carboplatin, cis-platin and oxaliplatin;
(xiv) compounds decreasing the protein kinase activity and further anti-angiogenic compounds, e.g. (i) compounds which decrease the activity of the Vascular Endothelial Growth Factor (VEGF) (b) the Epidermal Growth Factor (EGF), c-Src, protein kinase C, Platelet-derived Growth Factor (PDGF), Bcr-Abl tyrosine kinase, c-kit, Flt-3 and Insulin-like Growth Factor I Receptor (IGF-IR) and Cyclin-dependent kinases (CDKs); (ii) Imatinib, midostaurin, Iressa™ (ZD1839), CGP 75166, vatalanib, ZD6474, GW2016, CHIR-200131, CEP-7055/CEP-5214, CP-547632 and KRN-633;
(iii) thalidomide (THALOMID), celecoxib (Celebrex), SU5416 and ZD6126;
(xv) gonadorelin agonists, e.g. abarelix, goserelin and goserelin acetate;
(xvi) anti-androgens, e.g. bicalutamide (CASODEX™);
(xvii) bengamides;
(xviii) bisphosphonates, e.g. etridonic acid, clodronic acid, tiludronic acid, pamidronic acid, alendronic acid, ibandronic acid, risedronic acid and zoledronic acid;
(xix) antiproliferative antibodies, e.g. trastuzumab (Herceptin™), Trastuzumab-DM1, erlotinib (Tarceva™), bevacizumab (Avastin™), rituximab (Rituxan®), PRO64553 (anti-CD40) and 2C4 Antibody;
(x) temozolomide (TEMODAL®);
(xxi) Statins.

The structure of the active agents identified by code nos., generic or trade names may be taken from the actual edition of the standard compendium "The Merck Index" or from databases, e.g. Patents International (e.g. IMS World Publications).

In accordance with the foregoing the present invention further provides:
(6) A method as defined above comprising co-administration, e.g. concomitantly or in sequence, of a therapeutically effective amount of a) a compound of formula I or a pharmaceutically acceptable salt or hydrate thereof, and b) a second drug substance, said second drug substance being for example for use in any of the particular indications hereinbefore set forth;
(7) A combination, e.g. a kit, comprising a therapeutically effective amount of a compound of formula I or a pharmaceutically acceptable salt or hydrate thereof, and a second drug substance, said second drug substance being for example as disclosed above.

Where a compound of the invention is administered in conjunction with other immunosuppressive/immunomodulatory, anti-inflammatory or antineoplastic agent, e.g. as disclosed above, dosages of the co-administered drug or agent will of course vary depending on the type of co-drug or -agent employed, or the specific drug or agent used, or the condition being treated and so forth.

In another embodiment there is provided a method of manufacturing a compound of formula (I),

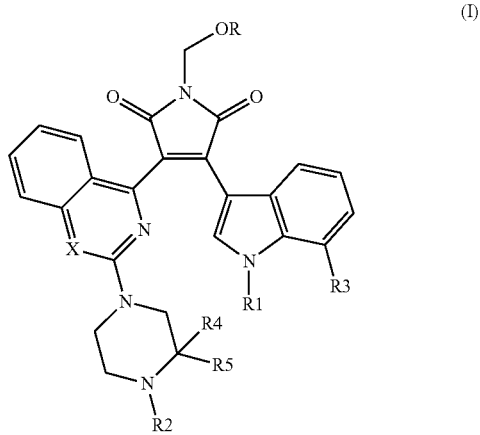

wherein X is CH or N; R is H or $PO_3H_2$; R1 is H or $C_{1-4}$alkyl; R2 is H or $C_{1-4}$alkyl; R3 is H, $C_{1-4}$alkyl, CN, Hal or OH; and R4 and R5 are independently from each other H, or $C_{1-4}$alkyl; or R4 and R5 form together with the carbon atom to which they are attached a 3-6 membered cycloalkyl group, comprising:

(a) optionally, for compounds wherein R1 and/or R2 are hydrogen, treating the maleimide of formula (Va) for example with di-tert-butyl dicarbonate in the presence or absence of a solvent such as THF or dichloromethane and/or a base such as triethyl amine, thereby yielding the maleimide of formula (Va) comprising tert-butoxycarbonyl groups instead of the hydrogens on R1 and/or R2 where appropriate;

(b) treating the optionally protected maleimide of formula (Va) for example with formaldehyde in the presence or absence of a solvent and/or a base such as potassium carbonate, thereby yielding an alcohol of formula (Vb), wherein R=H;

(c) optionally treating the alcohol of formula (Vb) for example with trichloroacetonitrile typically in the presence of a base, e.g. DBU or trimethylamine to form a reactive ester, followed by the treatment with a phosphorylating agent, e.g. with a phosphoric acid ester, e.g. with phosphoric acid di-tert-butyl ester typically in the presence of a base, e.g. DBU or trimethylamine, whereupon the resulting intermediate ester is treated with an appropriate acid, e.g. hydrochloric acid or TFA in the absence of presence of a solvent such as THF, dichloromethane, dichloroethane or the like to yield the final product in accordance to general formula (I), or as an alternative step (c)

alcohol of formula (Vb) may be reacted directly with a phosphoric acid ester, e.g. with phosphoric acid di-tert-butylester, e.g. under Mitsunobu reaction conditions to furnish the phosphoric acid ester, which may then be hydrolyzed, e.g. with trifluoroacetic acid, e.g. in dichloromethane to furnish the final product of formula (I).

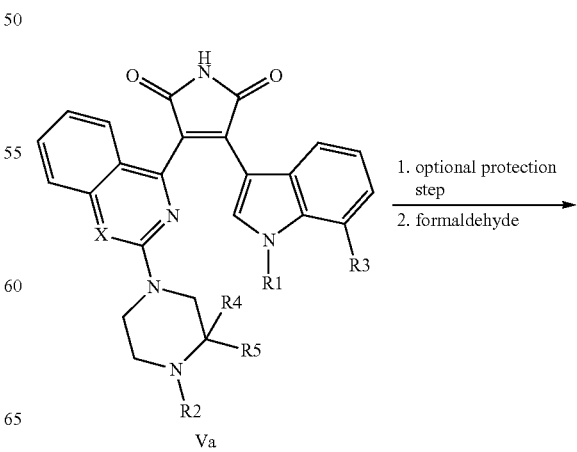

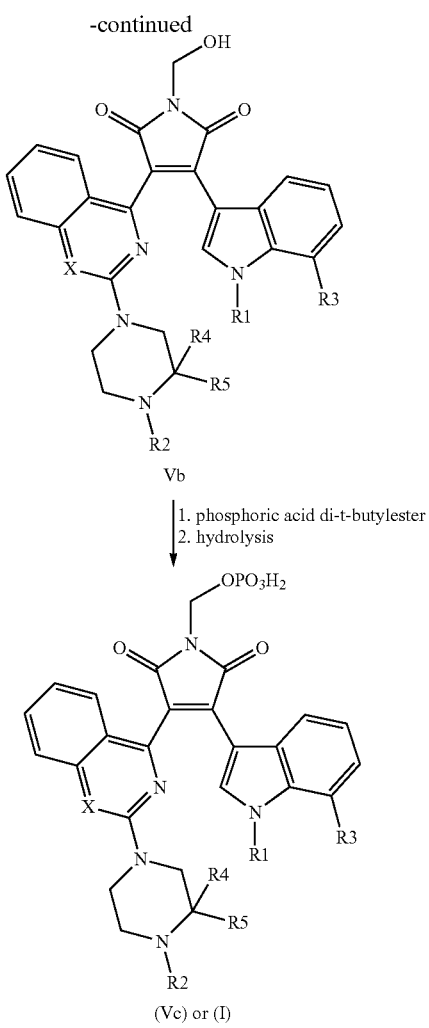

The invention claimed is:

1. A Method for the treatment of a disease or condition in which PKC activation plays a role or is implicated, in a subject in need thereof which comprises administering to the subject an effective amount of a compound of formula (I) or a pharmaceutically acceptable salt or hydrate thereof,

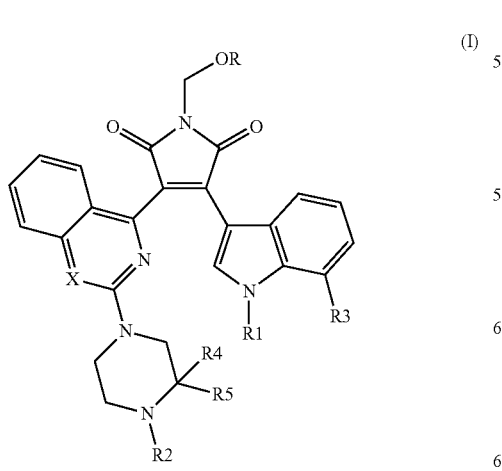

Wherein
X is CH or N;
R is H or $PO_3H_2$;
R1 is H; or $C_{1-4}$alkyl;
R2 is H; or $C_{1-4}$alkyl;
R3 is H; $C_{1-4}$alkyl; CN; Hal; or OH; and
R4 and R5 are independently from each other H, or $C_{1-4}$alkyl; or R4 and R5 form together with the carbon atom to which they are attached a 3-6 membered cycloalkyl group;
wherein the disease or condition is selected from psoriasis, acute or chronic rejection of organ or tissue allo- or xenografts and graft-versus-host disease and host-versus-graft disease.

2. The method according to claim 1, comprising administering to the subject an effective amount of a compound of Formula (I) or a pharmaceutically acceptable salt or hydrate thereof,
wherein
X is CH;
R is H;
R1 is H;
R2 is H; or $C_{1-4}$alkyl;
R3 is H; or $C_{1-4}$alkyl; and
R4 and R5 are independently from each other H; or R4 and R5 form together with the carbon atom to which they are attached a 3-6 membered cycloalkyl group.

3. The method according to claim 1, comprising administering to the subject an effective amount of a compound of Formula (I) or a pharmaceutically acceptable salt or hydrate thereof,
wherein
X is N;
R is $PO_3H_2$;
R1 is H;
R2 is H; or $C_{1-4}$alkyl;
R3 is H; and
R4 and R5 are independently from each other H; or R4 and R5 form together with the carbon atom to which they are attached a 3-6 membered cycloalkyl group.

4. The method according to claim 1, comprising administering to the subject an effective amount of a compound of formula (III)

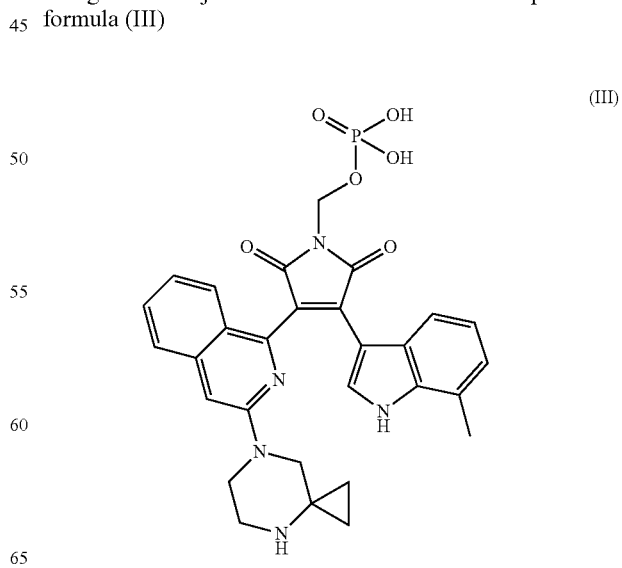

or a pharmaceutically acceptable salt or hydrate thereof.

5. The method according to claim 1, comprising administering to the subject an effective amount of a compound of Formula (I), which is phosphoric acid mono-[3-[3-(4,7-diaza-spiro[2.5]oct-7-yl)-isoquinolin-1-yl]-4-(7-methyl-1H-indol-3-yl)-2,5-dioxo-2,5-dihydro-pyrrol-1-ylmethyl]ester, mono-hydrate.

6. The method in accordance to claim 1, comprising administering to the subject an effective amount of a compound of Formula (I) which is 3-[3-(4,7-diaza-spiro[2.5]oct-7-yl)-isoquinolin-1-yl]-1-hydroxymethyl-4-(7-methyl-1H-indol-3-yl)-pyrrole-2,5-dione or a pharmaceutically acceptable salt thereof.

7. The method in accordance to claim 1, comprising administering to the subject an effective amount of a compound of Formula (I) which is phosphoric acid mono-{3-(1H-indol-3-yl)-4-[2-(4-methyl-piperazin-1-yl)-quinazolin-4-yl]-2,5-dioxo-2,5-dihydro-pyrrol-1-ylmethyl}ester or a pharmaceutically acceptable salt thereof.

\* \* \* \* \*